United States Patent

Naganuma et al.

[11] Patent Number: 5,600,005
[45] Date of Patent: Feb. 4, 1997

[54] PROCESS FOR PRODUCING TETRAKISFLOROPHENYLBORATE

[75] Inventors: Shoji Naganuma; Masami Watanabe, both of Sodegaura; Norio Tomotsu, Ichihara, all of Japan

[73] Assignee: Idemitsu Kosan Co., Ltd., Tokyo, Japan

[21] Appl. No.: 465,892

[22] Filed: Jun. 6, 1995

Related U.S. Application Data

[63] Continuation of Ser. No. 193,008, filed as PCT/JP93/00837 Jun. 22, 1993.

[30] Foreign Application Priority Data

Jun. 23, 1992 [JP] Japan ................................. 4-188834
Oct. 9, 1992 [JP] Japan ................................. 4-271356

[51] Int. Cl.$^6$ ..................................................... C07F 5/02
[52] U.S. Cl. ..................................................... 568/6
[58] Field of Search ...................................... 568/6

[56] References Cited

U.S. PATENT DOCUMENTS 4,224,256  9/1980  Klamann et al. ........................... 568/6
4,900,854  2/1990  Wintuton et al. .......................... 568/6
5,296,433  3/1994  Siedle et al. ............................... 568/6

FOREIGN PATENT DOCUMENTS 562897  9/1993  European Pat. Off. .................... 568/6

OTHER PUBLICATIONS

Maruyen, Organometabir chem., vol. 15, p. 307 (1976).

*Primary Examiner*—James H. Reamer
*Attorney, Agent, or Firm*—Oblon, Spivak, McClelland, Maier & Neustadt, P.C.

[57] ABSTRACT

A process for preparing a tetrakisfluorophenylborate which is useful as a catalyst component for the polymerization of olefins or as a raw material for synthesizing the same, efficiently at a high productivity per unit amount of a solvent and at a high yield. A mixed solvent of ether and an aliphatic hydrocarbon is used as a reaction solvent for preparing tetrakisphenylborate according to the following reaction formula, $$4M^4\text{—}C_6Y^3{}_5 + BCl_3 \rightarrow M^4B(C_6Y^3{}_5)_4$$

wherein $M^4$ is an alkali or alkaline earth metal, or represents $R^6{}_2Al$, wherein $R^6$ is an alkyl group, and $Y^3$ is a hydrogen atom or a halogen atom.

8 Claims, No Drawings

PROCESS FOR PRODUCING TETRAKISFLOROPHENYLBORATE

This application is a Continuation of application Ser. No. 08/193,008, filed on Feb. 17, 1994, now abandoned, filed as International Application Number PCT/JP93/00837, filed Jun. 12, 1993.

FIELD OF THE INVENTION

The present invention relates to an improvement in a process for preparing a tetrakisphenylborate, and, more particularly, to a process for preparing a tetrakisphenylborate, particularly a tetrakisfluorophenylborate, which is highly pure, has a superior olefin polymerization activity, and is useful as a catalyst component for the polymerization of olefins, such as α-olefins and styrene monomers, or as a raw material for synthesizing the same, efficiently at a high productivity per unit amount of a solvent and at a high yield.

BACKGROUND ART

Catalysts consisting of a zirconium compound and aluminoxane are known to exhibit a high polymerization activity in the polymerization of olefins, such as α-olefins (Japanese Patent Application Laid-open (kokai) No. 19309/1983). This method has a drawback in that a sufficient activity cannot be obtained unless expensive aluminoxane is used at a high ratio for a transition metal compound. In addition, not only preparing aluminoxane involves danger because of use of highly reactive trimethylaluminum to be reacted with water, but also its isolation from the reaction product as a single substance is difficult. Thus, controlling the catalyst for preparing a product with a stable quality has been difficult.

A method of using a homogeneous polymerization catalyst containing a reaction product of a transition metal compound, a coordination complex compound, and an organo-aluminum compound, as a major component, has been disclosed (Japanese Patent Application Laid-open (kokai) No. 207704/1991). As the coordination complex compound, a compound which can form an ionic complex by the reaction with a transition metal compound is used. Tetrakisphenylborate compounds are known as typical compounds among such coordination complex compounds.

This homogeneous catalyst containing the reaction product of such a tetrakisphenylborate complex compound and a transition metal compound as a major component is economical, because it requires no use of or only a small amount of expensive components such as aluminoxane. In addition, this catalyst can efficiently produce polymers having various characteristics. Because of these reasons, its active use as a catalyst for the polymerization of olefins, such as α-olefins and styrene monomers, is recently ongoing.

As raw materials for the synthesis of said tetrakisphenylborate complex compounds, tetrakisphenylborates, for example, lithium(pentafluorophenyl)borate [Li[B($C_6F_5$)$_4$]], can be used. A process according to the following reaction formulas is known as a process for preparing these tetrakisphenylborates [J. Organomet Chem., 2, 245–250 (1964)].

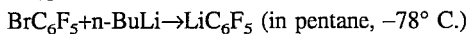
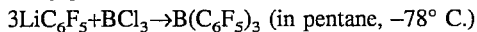
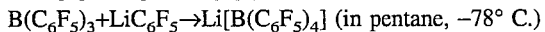

This process has drawbacks in that a complicated procedure is required for the synthesis of the final product, Li[B($C_6F_5$)$_4$], after isolation of the intermediate product, B($C_6F_5$)$_3$, and further that the reaction is delayed and the yield is reduced due to the reaction which takes place between solid LiC$_6$F$_5$, which is produced by the use of pentane as a solvent, and liquid BCl$_3$.

Another process, in which the reaction proceeds according to the following formulas, has been reported [Report from Asahi Glass Co., Ltd., Industrial Technology Motivation Institution, 42, 137 (1983)].

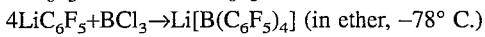

However, this process has a drawback of a low yield because of the use of ether as a solvent with which BCl$_3$ produces a complex, which is insoluble in ether.

DISCLOSURE OF THE INVENTION

According to the present invention, a process for preparing a tetrakisfluorophenylborate is provided, which comprises a first step in which the following reactions (1) and (2) are carried out in sequence and a second step in which the following reactions (3) and (4) are carried out in sequence, First Step:

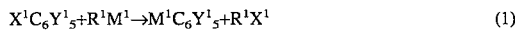  (1)

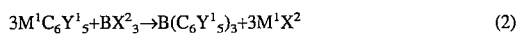  (2)

Second Step:

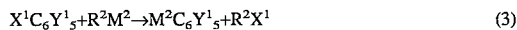  (3)

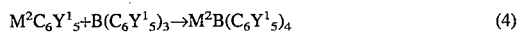  (4)

wherein $X^1$ and $X^2$ individually represent a halogen atom; Y represents a hydrogen atom or a fluorine atom, provided that 2 to 5 Ys among five Ys are fluorine atoms; $R^1$ and $R^2$ individually indicate an alkyl group or an aryl group; and $M^1$ and $M^2$ individually are an alkali or alkaline earth metal, or represent $R^3{}_2Al$, provided that $R^3$ is an alkyl group; and wherein the molar ratio of $M^1C_6Y^1{}_5$ and $BX^2{}_3$ in the above reaction of formula (2) is $3/2.5 \leq M^1C_6Y^1{}_5/BX^2{}_3 \leq 3/1.05$.

Further, a process for preparing a tetrakisfluorophenylborate is provided, which comprises carrying out the following reactions (5) and (6) in sequence using an aliphatic hydrocarbon solvent.

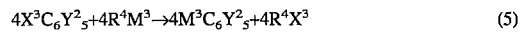  (5)

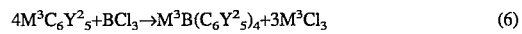  (6)

wherein $X^3$ represents a halogen atom; $Y^2$ represents a hydrogen atom or a fluorine atom, provided that 2 to 5 $Y^2$s among five $Y^2$s are fluorine atoms; $R^4$ indicates an alkyl group or an aryl group; and $M^3$ is an alkali or alkaline earth metal, or represents $R^5{}_2Al$, provided that $R^5$ is an alkyl group.

Still further, a process for preparing a tetrakisphenylborate is provided, which comprises carrying out the following reaction (7),

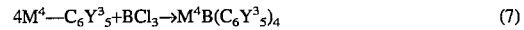  (7)

wherein $M^4$ is an alkali or alkaline earth metal, or represents $R^6{}_2Al$, provided that $R^6$ is an alkyl group, and $Y^3$ represents a hydrogen atom or a halogen atom, in a mixed solvent of ether and an aliphatic hydrocarbon.

Furthermore, a process for preparing a tetrakisfluorophenylborate is provided, which comprises adding a hydrocarbon solvent to the tetrakisfluorophenylborate to which a Lewis base is coordinated and removing the Lewis base by concentrating or drying it under reduced pressure.

Provided also is a process for preparing a tetrakisfluorophenylborate, wherein said tetrakisfluorophenylborate to which a Lewis base is coordinated is a compound produced by said process.

Further provided is a process for the purification of a tetrakisfluorophenylborate, which comprises dissolving the tetrakisfluorophenylborate in a solvent having an SP value of 15 or larger and 30 or smaller and depositing it from water or an aliphatic hydrocarbon solvent.

Still further provided is a process for the purification of a tetrakisfluorophenylborate, wherein said tetrakisfluorophenylborate which is to be purified is the tetrakisfluorophenylborate prepared by said process.

Lithium tetrakis(pentafluorophenyl)borate, sodium tetrakis(pentafluorophenyl)borate, diisobutylaluminum tetrakis(pentafluorophenyl)borate, diethylaluminum tetrakis(pentafluorophenyl)borate, and the like are given as examples of the tetrakisphenylborates obtained by the process of the present invention. These borates are suitable for use as a coordination complex compound, which is a catalyst component for the synthesis of olefin polymerization, or as a raw material for the synthesis of this coordination complex compound. For example, these are used as a raw material for the synthesis of the following coordination complex compounds:
triethylammonium tetrakis(pentafluorophenyl)borate,
tri-n-butylammonium tetrakis(pentafluorophenyl)borate,
triphenylammonium tetrakis(pentafluorophenyl)borate,
tetrabutylammonium tetrakis(pentafluorophenyl)borate,
(tetraethylammonium)tetrakis(pentafluorophenyl)borate,
[methyltri(n-butyl)ammonium]tetrakis(pentafluorophenyl)borate,
[benzyltri(n-butyl)ammonium]tetrakis(pentafluorophenyl)borate,
methyldiphenylammonium tetrakis(pentafluorophenyl)borate,
methyltriphenylammonium tetrakis(pentafluorophenyl)borate,
dimethyldiphenylammonium tetrakis(pentafluorophenyl)borate,
anilinium tetrakis(pentafluorophenyl)borate,
(N-methylanilinium)tetrakis(pentafluorophenyl)borate,
(N,N-dimethylanilinium)tetrakis(pentafluorophenyl)borate,
(N,N,N-trimethylanilinium)tetrakis(pentafluorophenyl)borate,
(m-nitroanilinium)tetrakis(pentafluorophenyl)borate,
(p-bromoanilinium)tetrakis(pentafluorophenyl)borate,
pyridinium tetrakis(pentafluorophenyl)borate,
(p-cyanopyridinium)tetrakis(pentafluorophenyl)borate,
(N-methylpyridinium)tetrakis(pentafluorophenyl)borate,
(N-benzylpyridinium)tetrakis(pentafluorophenyl)borate,
(o-cyano-N-methylpyridinium)tetrakis(pentafluorophenyl)borate,
(p-cyano-N-methylpyridinium)tetrakis(pentafluorophenyl)borate,
(p-cyano-N-benzylpyridinium)tetrakis(pentafluorophenyl)borate,
trimethylsulfonium tetrakis(pentafluorophenyl)borate,
benzyldimethylsulfonium tetrakis(pentafluorophenyl)borate,
tetraphenylphosphonium tetrakis(pentafluorophenyl)borate,
triphenylphosphonium tetrakis(pentafluorophenyl)borate,
ferrocenium tetrakis(pentafluorophenyl)borate,
(1,1'-dimethylferrocenium)tetrakis(pentafluorophenyl)borate,
decamethylferrocenium tetrakis(pentafluorophenyl)borate,
acetylferrocenium tetrakis(pentafluorophenyl)borate,
formylferrocenium tetrakis(pentafluorophenyl)borate,
cyanoferrocenium tetrakis(pentafluorophenyl)borate,
silver tetrakis(pentafluorophenyl)borate,
trytyl tetrakis(pentafluorophenyl)borate,
(tetraphenylporphyrine manganese)tetrakis(pentafluorophenyl)borate,
(tetraphenylporphyrine iron chloride)tetrakis(pentafluorophenyl)borate,
(tetraphenylporphyrine zinc)tetrakis(pentafluorophenyl)borate,
and the like.

The specific embodiments of the present invention will be illustrated in detail hereinafter as first to seven inventions in sequence.

1. First Invention

The first invention (a process) comprises, as mentioned above, a first step in which the aforementioned reactions (1) and (2) are carried out in sequence and a second step in which the aforementioned reactions (3) and (4) are carried out in sequence, and is characterized in that the molar ratio of $M^1C_6Y^1_5$ and $BX^2_3$ in the reaction of formula (2) is $3/2.5 \leq M^1C_6Y^1_5/BX^2_3 \leq 3/1.05$.

Here, given as halogen atoms for $X^1$ in $X^1C_6Y^1_5$ used in the reaction of formula (1) are iodine, bromine, chlorine, fluorine, and the like, with preferred halogen atoms being bromine or chlorine. 3,5-Difluorophenyl group, 3,4,5-trifluorophenyl group, pentafluorophenyl group, and the like are given as $C_6Y^1_5$, with pentafluorophenyl group being preferred. Given as alkyl groups for $R^1$ in $R^1M^1$ used in reaction (1) are $C_1$–$C_{20}$ alkyl groups, such as methyl, n-butyl, sec-butyl, tert-butyl, and isobutyl groups; as aryl groups are $C_6$–$C_{20}$ aryl groups, such as phenyl group; and as alkali metals or alkaline earth metals for $M^1$ are lithium, sodium, potassium, and magnesium bromide. As alkyl groups for $R^3$, given are the same alkyl groups for $R^1$. As $R^3_2Al$, diisobutylaluminum, diethylaluminum, and the like are given.

Also, given as halogen atoms for $X^2$ in $BX^2_3$ used in the reaction of formula (2) are iodine, bromine, chlorine, fluorine, and the like. $BX^2_3$ may contain an electron donating complex, such as trifluoroboranediethyl ether complex ($BF_3 \cdot OEt_2$).

Specifically, as $X1C_6Y^1_5$, bromopentafluorobenzene, chloropentafluorobenzene, bromo-3,5-difluorobenzene, and the like; as $R^1M^1$, n-butyl lithium, methyl lithium sec-butyl lithium, triisobutyl aluminum, and the like; and as $BX^2_3$, boron trichloride, boron tribromide, boron trifluoride, boron trifluoride-diethyl ether complex, and the like, can be preferably used.

Although there are no specific limitations to the methods and conditions for carrying out the reactions of formulas (1) and (2), for example, the following methods and conditions can be adopted.

Reaction of formula (1)

First, a solvent (hereinafter a solvent used in reactions of formulas (1) and (2) are called solvent (a)) and 3x mol of $X^1C_6Y^1_5$ are mixed. Linear or cyclic aliphatic hydrocarbons, such as pentane, hexane, and cyclohexane, are preferably used as solvent (a). The ratio of $X^1C_6Y^1_5$ to solvent (a) ($X^1C_6Y^1_5$/solvent (a)) is preferably 0.1–1 mol/litter.

Next, the mixture of solvent (a) and $X^1C_6Y^1_5$ is cooled to $-30°$ C. or lower, preferably to $-60°$ C. or lower, and a solution of 2.7x–3.6x mol of $R^1M^1$ dissolved in solvent (a) is added to this mixture while stirring. In this instance, the ratio of $R^1M^1$ for solvent (a) in this solution ($R^1M^1$/solvent (a)) is preferably 0.5–3 mol/litter.

Then, the mixture is stirred for a prescribed period of time (normally about 2 hours) while maintaining the above temperature to produce $M^1C_6Y^1_5$ and $R^1X^1$ in solvent (a).
Reaction of formula (2)

A solution of 1.0x–2.5x mol of $BX^2_3$ dissolved in solvent (a) is added to said solvent (a) in which $M^1C_6Y^1_5$ and $R^1X^1$ have been produced. In this instance, the ratio of $BX^2_3$ to solvent (a) in said solution ($BX^2_3$/solvent (a)) is preferably 0.1 mol/litter or greater.

Thereafter, the mixture is stirred for a prescribed period of time (normally about 2 hours) while maintaining the above temperature to produce $B(C_6Y^1_5)_3$ in solvent (a).
Isolation of $B(C_6Y^1_5)_3$ Upon completion of the reaction of formula (2), beside $B(C_6Y^1_5)_3$, there are by-products in solution (a), such as $BX^2_3$, $BX^2_2C_6Y^1_5$, $BX^2(C_6Y^1_5)_2$, $M^1X^2$, $R^1X^1$, and $M^1[B(C_6Y^1_5)_4]$. Therefore, solvent (a) is cooled to −30° C. or lower, preferably to −60° C. or lower, and filtered to separate these by-products. $BX^2_3$, $BX^2_2C_6Y^1_5$, $BX^2B(C_6Y^1_5)_3$, $M^1[B(C_6Y^1_5)_4]$, and $M^1X^2$ ($M^1$: an alkali metal) can be removed as a solid phase by this procedure.

Next, solvent (a) is added to the solid phase thus obtained. In this instance, the amount of solvent (a) to be added to the solid phase is preferably such that the amount of $B(C_6Y^1_5)_3$ in solvent (a) ($B(C_6Y^1_5)_3$/solvent (a)) is 0.1–1 mol/litter.

Thereafter, the temperature of solvent (a) is raised to −20° to 30° C. preferably −10° to 20° C. and the solvent (a) is separated by filtration. $B(C_6Y^1_5)_3$ is isolated in the liquid phase, and $M^1[B(C_6Y^1_5)_4]$ and $M^1X^2$ ($M^1$: an alkali metal) are separated as the solid phase by this procedure.

In the reaction of formula (3), the same compound as used the reaction of formula (1) is used as $X^1C_6Y^1_5$. As $R^2$ and $M^2$ in $R^2M^2$ used for the reaction of formula (3), the same groups as previously given for $R^1$ and $M^1$ are respectively used.

Specifically, n-butyl lithium, methyl lithium, sec-butyl lithium, triisobutyl aluminum, and the like can be preferably used as the $R^2M^2$.

Although there are no specific limitations to the methods and conditions for carrying out the reactions of formulas (3) and (4), the following methods and conditions can be adopted.
Reaction of formula (3)

First, a solvent (hereinafter a solvent mixed with $X^1C_6Y^1_5$ in reaction of formula (3) is called solvent (b)) and y mol of $X^1C_6Y^1_5$ are mixed. Although there are no specific limitations to the solvent (b) used here, it is necessary that the solvent dissolve $M^2C_6Y^1_5$. Ether-type solvents, such as diethyl ether and tetrahydrofuran, are preferable. A preferable amount of solvent (b) used is such that the ratio by volume of solvent (a) containing $B(C_6Y^1_5)_3$, used in the first step, to solvent (b) (solvent (a)/solvent (b)) is 1/1–100/1, and particularly 5/1–10/1.

Next, the mixture of solvent (b) and $X^1C_6Y^1_5$ is cooled to −30° C. or lower, preferably to −60° C. or lower, and a solution of 0.9y–1.2y mol of $R^1M^1$ dissolved in a solvent ((hereinafter a solvent mixed with $R^1M^1$ in the reaction of formula (3) is called solvent (c)) is added to this mixture while stirring. In this instance, the ratio of $R^1M^1$ to solvent (c) in this solution ($R^1M^1$/solvent (c)) is preferably 0.5–3 mol/litter. As solvent (c), the same solvents used as solvent (a) are given as examples. Then, the mixture is stirred for a prescribed period of time (normally about 30 minutes) while maintaining the above temperature, to produce $M^2C_6Y^1_5$ and $R^2X^1$ in a mixed solvent of solvent (b) and solvent (c).
Reaction of formula (4)

A mixed solution of solvent (b) and solvent (c) in which $M^2C_6Y^1_5$ and $R^2X^1$ have been produced according to the reaction of formula (3) is cooled to −30° C. or lower, preferably to −60° C. or lower, and this solution is added to a solution of $B(C_6Y^1_5)_3$ dissolved in solvent (a), which has been isolated in the first step, at a temperature of −20° to 30° C., preferably −10° to 20° C.

Thereafter, the mixture is stirred for a prescribed period of time (normally about 30 minutes) at a temperature of −20° to 30° C., preferably −10° to 20° C. A complex of $M^2B(C_6Y^1_5)_4$ and solvent (b) is deposited as a solid by this procedure. The solid complex, $[M^2B(C_6Y^1_5)_4]$-[solvent (b)], is collected by removing the solvent by filtration.

The fluorine-substituted tetraphenylborate obtained by the process of the present invention may be a compound to which a solvent used in the synthesis or the purification has been coordinated.

Both the above reactions of formulas (3) and (4) are preferably carried out in an inert gas stream.

The yield of the complex $[M^2B(C_6Y^1_5)_4]$-[solvent (b)] (z mol) (based on $B(C_6Y^1_5)_3$ (y mol): (z/y)×100%) is 55% or higher according to this embodiment.

The overall yield of the complex $[M^2B(C_6Y^1_5)_4]$-[solvent (b)] (z mol) (based on $X^1C_6Y^1_5$ (x mol): (z/x)×100%) is normally 30% or higher according to this embodiment.

In this first invention the molar ratio of $M^1C_6Y_5/BX^2_3$ should be 3/2.5 to 3/1.05 in the above reaction of formula (2), and, preferably, $B(C_6Y_5)_3$ is purified by removing by-products from the reaction mixture obtained by the reaction of formula (2), and this purified compound is used in the subsequent reaction of formula (4). This procedure ensures the efficient preparation of $M^2B(C_6Y_5)_4$ at a high yield of 30% or higher based on $X^1C_6Y_5$, as mentioned above. On the other hand, when the amount of $M^1C_6Y^1_5/BX^2_3$ (in molar ratio) is outside the above range, it is difficult to obtain the fluorine-substituted tetraphenylborate at a high yield. A more preferable range of $M^1C_6Y_5/BX^2_3$ (molar ratio) is 3/2.0 to 0–3/1.1.
2. Second Invention The second invention (a process) comprises, as mentioned above, carrying out the aforementioned reactions (5) and (6) in sequence using an aliphatic hydrocarbon solvent as a reaction solvent.

In this instance, given as halogen atoms for $X^3$ in $X^3C_6Y^2_5$ used in the reaction of formula (5) are iodine, bromine, chlorine, fluorine, and the like, with preferred halogen atoms being bromine or chlorine. 2-Fluorophenyl group, 3-fluorophenyl group, 4-fluorophenyl group, 3,5-difluorophenyl group, 2,4-difluorophenyl group, 2,5-difluorophenyl group, 3,4,5-trifluorophenyl group, pentafluorophenyl group, 3,5-bis(trifluoromethyl)phenyl group, and the like are given as examples of $C_6Y^2_5$, with pentafluorophenyl group being preferred. Given as examples of alkyl groups for $R^4$ in $R^4M^3$ used in the reaction of formula (5) are $C_1$–$C_{20}$ alkyl groups, such as methyl, n-butyl, sec-butyl, tert-butyl, and isobutyl groups; as aryl groups for $R^4$ are $C_6$–$C_{20}$ aryl groups, such as phenyl group; and as alkali metals or alkaline earth metals for $M^3$ are lithium, sodium, potassium, and magnesium bromide, with lithium being particularly preferred. As alkyl groups for $R^3$, given are the same alkyl groups for $R^4$, and as $R^3_2Al$, diisobutylaluminum, diethylaluminum, and the like are given as examples.

Specifically, as $X^3C_6Y^2_5$, bromopentafluorobenzene, chloropentafluorobenzene, bromo-3,5-difluorobenzene, bromo-3,5-bis(trifluoromethyl)benzene, and the like; and as $R^4M^3$, n-butyl lithium, tert-butyl lithium, methyl lithium, sec-butyl lithium, triisobutyl aluminum, and the like, can be preferably used.

Although there are no specific limitations to the method and conditions for carrying out the reactions of formulas (5)

and (6), for example, the following method and conditions can be adopted.

Reaction of formula (5)

First, a solvent (a) (hereinafter a solvent used in reactions of formulas (5) and (6) is called solvent (a)) and 4x mol of $X^3C_6Y^2_5$ are mixed.

Next, a solution of 3.6x–4.8x mol of $R^4M^3$ dissolved in solvent (a) is added to the mixture of solvent (a) and $X^3C_6Y^2_5$.

Then, the mixture is stirred for a prescribed period of time (normally about 2 hours) while maintaining the above temperature to produce $M^3C_6Y^2_5$ and $R^4X^3$ in solvent (a).

Reaction of formula (6)

A solution of 0.9x to 1.1x mole of $BX^4_3$, for example, $BCl_3$, dissolved in solvent (a), is added to solvent (a) in which $M^3C_6Y^2_5$ and $R^4X^3$ have been produced (−30° C. or lower, preferably −60° C. or lower). It is desirable that the ratio of solvent (a) to $BCl_3$, ($BCl_3$/solvent (a)), in said solution be 0.1 mol/litter or more.

Thereafter, the mixture is stirred for a prescribed period of time (normally about two hours) while maintaining the above temperature, to produce $M^3B(C_6Y^2_5)_4$ in solvent (a).

After the completion of the reaction of formula (6), the temperature of solvent (a) is raised to 0° to 30° C., preferably 0° to 20° C., and the solvent (a) is separated by filtration.

The tetrakisfluorophenylborate obtained by the process of the present invention may be a compound to which a solvent used in the synthesis or the purification has been coordinated.

The yield of the complex $[M^3B(C_6Y^2_5)_4]$-[solvent (d)] (y mol) (based on $B(C_6Y^2_5)_3$ (x mol): (y/x)×100%) is 30% or higher according to this embodiment.

3. Third Invention

The third invention (a process), as mentioned above, is characterized by using a mixed solvent of ether and an aliphatic hydrocarbon as a reaction solvent when carrying out the reaction of formula (7).

In the third invention, $M^4—C_6Y^3_5$ and boron trichloride ($BCl_3$) are reacted in the solvent to produce a tetrakisphenylborate, which consists of $M^4B(C_6Y^3_5)_4$. $M^4$ in $M^4—C_6Y^3_5$, which is a part of the raw materials, is an alkali metal such as lithium, sodium, or potassium; an alkaline earth metal such as calcium, magnesium, and strontium; or a group $R_2Al$ (R is an alkyl group, especially a $C_1$–$C_8$ alkyl group), with a preferred group being an alkali metal, in particular, lithium. Although $Y^3$ represents a hydrogen atom or a halogen atom, at least one of $Y^3$s is preferably a halogen atom, in particular a fluorine atom. Given as preferred examples of $M^4—C_6Y^3_5$ are $M^4—C_6F_5$, $M^4—C_6HF_4$, $M^4—C_6H_2F_3$, $M^4—C_6H_3F_2$, and $M^4—C_6H_4F$.

The method of preparing $M^4—C_6Y^3_5$ is not particularly limited and conventionally known methods can be used.

For example, when $LiC_6F_5$ is produced as $M^4—C_6Y^3_5$, $BrC_6F_5$ and n-butyl lithium may be reacted in a suitable solvent. As a suitable solvent used here, the same a mixed solvent of ether and an aliphatic hydrocarbon, the same solvent which is described below, is advantageous from the aspect of the reaction.

It is essential to use a mixed solvent of ether and an aliphatic hydrocarbon as a reaction solvent for the reaction of $M^4—C_6Y^3_5$ and boron trichloride in the present invention. If either ether or an aliphatic hydrocarbon is used singly as a reaction solvent, the object of the present invention cannot be achieved because the yield of the target tetrakisphenylborate is low.

Given as examples of ethers are aliphatic ethers such as diethyl ether, dipropyl ether, propyl methyl ether, propyl ethyl ether, dibutyl ether, butyl methyl ether, butyl ethyl ether, and butyl propyl ether. Either one of them may be used singly or two or more of them may be used in combination. On the other hand, given as examples of aliphatic hydrocarbons are $C_5$–$C_{12}$ paraffins, such as pentane and hexane; and $C_5$–$C_8$ cycloparaffins, such as cyclohexane and cycloheptane. They may be used either singly or two or more of them may be used in combination.

Although there are no particular limitations to the proportion of said ethers and aliphatic hydrocarbons, it is desirable that the ratio by weight be in the range of 100:1 to 1:100. The amount of ethers mixed is advantageously equimolar to or greater than boron trichloride.

A reaction temperature below −20° C. may be used without specific limitation, with a temperature −50° C. or below being preferred. Although there are no particular restrictions to the reaction pressure, the reaction in an inert gas atmosphere, such as a nitrogen gas atmosphere, is preferred.

Tetrakisphenylborate consisting of $M^4B(C_6Y^3_5)$, wherein $M^4$ and $Y^3$ are the same as defined above, can be obtained at a high yield in this manner. Ionic complexes between an isomer, such as $B(C_6F_5)_4—$, $B(C_6HF_4)_4—$, $B(C_6H_2F_3)_4—$, $B(C_6H_3F_2)_4—$, and $B(C_6HF_4)_4—$, or the like, and an alkali metal, an alkaline earth metal, or $R^2Al$ (wherein R is an alkyl group) are given as specific examples of said tetrakisphenylborate.

4. Fourth Invention

The fourth invention (a process), as mentioned above, is characterized by adding a hydrocarbon solvent to a tetrakisfluorophenylborate to which a Lewis base is coordinated and removing the Lewis base by concentrating or drying it under reduced pressure.

Here, the Lewis base (L) which is coordinated to the tetrakisfluorophenylborate and which is to be removed by the process means a compound containing an element which comprises a lone pair, such as oxygen, sulfur, nitrogen, and phosphorus.

Given as specific examples of such Lewis bases are, as those containing oxygen, methanol, ethanol, diethyl ether, tetrahydrofuran, acetone, ethyl acetate, and methyl ethyl ketone; as those containing sulfur, diethyl thioether, tetrahydrothiophene, and dimethylsulfoxide; as those containing nitrogen, triethylamine, dimethylaniline, pyridine, piperidine, and acetonitrile; and as those containing phosphorus, triethylphosphine and trimethylphosphine.

Although there are no specific limitations as to the hydrocarbon solvents used when the Lewis base is removed by concentration or drying under reduced pressure, those having a boiling point of 80° C. or higher and 180° C. or lower are preferred.

Specifically, aromatic compounds, such as benzene, toluene, xylenes, trimethylbenzenes, and ethylbenzenes; and aliphatic hydrocarbons, such as hexane and heptane, are given, with preferred solvents being toluene and xylenes.

The solvent can be suitably selected depending on the types of Lewis bases which are coordinated.

Regarding the conditions under which the concentration or the drying under reduced pressure is carried out are pressure of 1 mmHg or below, preferably 0.5 mmHg or below, and a temperature of −20° C. to 100° C., preferably 0° C. to 80° C.

This concentration or drying under reduced pressure may be carried out only once or may be repeated two or more times. The quantity of the solvent is preferably reduced to ½ by the concentration or the drying.

The proportion in molar ratio of the tetrakisfluorophenylborate and the hydrocarbon solvent used in this invention (hydrocarbon solvent/tetrakisfluorophenylborate) is 10 to 1,000, and preferably 50 to 200.

Further, it is desirable that the purity of the tetrakisfluorophenylborate obtained by this invention satisfy the inequality 0≦Lewis acid/tetrakisfluorophenylborate≦0.5, and preferably 0≦Lewis acid/tetrakisfluorophenylborate<0.1.

5. Fifth Invention

The fifth invention (a process), as mentioned above, is characterized by using the tetrakisfluorophenylborate prepared in either one of processes of the first to third inventions as the material for the fourth invention.

6. Sixth Invention

The sixth invention (a purification process), as mentioned above, is characterized by dissolving a tetrakisfluorophenylborate in a solvent having an SP value of 15 or larger and 30 or smaller and depositing it from water or an aliphatic hydrocarbon solvent.

Tetrakisfluorophenylborates immediately after the synthesis are colored and contain residual salts. Because of this, they cause problems, such as coloration of the polymer, corrosion of molds when the polymer is molded, and the like, if they are used as are. This sixth invention relates to a purification process for the tetrakisfluorophenylborates by removing impurities therefrom.

Illustrating the sixth invention in detail, a tetrakisfluorophenylborate after the synthesis contains by-products, including salts such as lithium chloride, and decomposed substances such as n-butyl lithium, $LiC_6F_5$, $B(C_6F_5)_3$, and $MgBrC_6F_5$. In this invention, in order to remove these impurities the tetrakisfluorophenylborate as produced is first dissolved in a solvent having an SP value of 15 or larger and 30 or smaller. Used as this solvent are ethers, such as diethyl ether, dibutyl ether, ethyl butyl ether, methyl butyl ether, and tetrahydrofuran; alcohols, such as methanol, ethanol, propanol, and buthanol; ketones, such as acetone, methyl ethyl ketone, or diethyl ketone; and halogenated hydrocarbons, such as dichloromethane, chloroform, chloroethane, dichloroethane, and trichloroethane. Two or more of these solvents may be used together. Then, the tetrakisfluorophenylborate is deposited from water or an aliphatic hydrocarbon solvent.

7. Seventh Invention

The seventh invention (a purification process), as mentioned above, is characterized by using the tetrakisfluorophenylborate prepared either the process of the fourth or fifth invention as the material for the sixth invention.

As illustrated above, the processes for the preparation and purification of a tetrakisfluorophenylborate of the present invention can produce a high purity tetrakisphenylborate, especially a high purity tetrakisfluorophenylborate, having a superior olefin polymerization activity and useful as a catalyst component for the polymerization of olefins or as a raw material for synthesizing the same, efficiently at a high productivity per unit amount of a solvent and at a high yield.

BEST MODE FOR CARRYING OUT THE INVENTION

The present invention will be illustrated in detail by way of examples, which shall not be limiting of the present invention.

EXAMPLE 1

Lithium tetrakis(pentafluorophenyl)borate was synthesized by the following first and second steps. All the following steps were carried out under a nitrogen gas stream.

(I) Synthesis of tris(pentafluorophenyl)boron (the first step)

24.7 g of bromopentafluorobenzene ($BrC_6F_5$) (F.W. 246.97, 0.1 mol) and 500 ml of dry hexane were mixed and cooled to −70° C. To the mixture was added slowly and dropwise a solution of 0.1 mol of n-butyl lithium in hexane (1.5 mol/l) while stirring. The stirring was continued at −70° C. for two hours to react the mixture.

Then, a solution of 0.04 mol of boron trichloride dissolved in hexane (1.35 mol/l) was rapidly added dropwise to the reaction solution. The stirring was continued at −70° C. for two hours to react the mixture.

The reaction solution was filtered at −70° C. to remove the hexane layer (in which impurities were dissolved). 500 ml of hexane was added to the solid thus obtained and the mixture was allowed to come to the room temperature. 12.1 g of tris(pentafluorophenyl)boron ($B(C_6F_5)_3$) was contained in the hexane layer (containing no impurities dissolved) obtained by the further removal of a solid (yield based on $BrC_6F_5$: 71%).

(II) Synthesis of lithium tetrakis(pentafluorophenyl)borate (the second step)

5.85 g (0.0237 mol) of bromopentafluorobenzene and 100 ml of dry diethyl ether were mixed and cooled to −70° C. To the mixture was added slowly and dropwise a solution of 0.0237 mol of n-butyl lithium in hexane (1.5 mol/l) while stirring. The stirring was continued at −70° C. for 30 minutes to react the mixture.

Then, the reaction solution (−70° C.) was slowly added dropwise to a solution of 12.1 g of tris(pentafluorophenyl)boron, obtained in (1) above, dissolved in hexane (500 ml, room temperature) and the mixture was stirred for 30 minutes at room temperature. 17.1 g of a white solid of lithium tetrakis(pentafluorophenyl)borate-diethyl ether complex ($LiB(C_6F_5)_4 \cdot OEt_2$) was obtained by removing the solvent and drying the residue under reduced pressure (yield: 95%).

The lithium tetrakis(pentafluorophenyl)borate-diethyl ether complex was obtained by steps (I) and (II) at an overall yield of 67.5% based on the raw material $BrC_6F_5$.

(III) Synthesis of dimethylanilinium tetrakis(pentafluorophenyl)borate 2 g ($2.92 \times 10^{-3}$ mol) of the lithium tetrakis(pentafluorophenyl)borate-diethyl ether complex was dissolved in 70 ml of water and 0.44 g ($2.78 \times 10^{-3}$ mol) of dimethylanilinium chloride was added to the solution, followed by stirring at room temperature for one hour. The solid thus obtained was thoroughly washed with water and hexane.

The above solid was dissolved in 20 ml of acetone, and this acetone solution was poured into a large quantity of water to re-precipitate the solid. The solid component was collected by filtration. 10 ml of dry toluene was added to the solid component and the mixture was dried under reduced pressure, to obtain 2.01 g of dimethylanilinium tetrakis(pentafluorophenyl)borate ($[PhNMe_2H][B(C_6F_5)_4]$) (yield: 86%). No Lewis base was coordinated to this complex.

(IV) Polymerization using dimethylanilinium tetrakis(pentafluorophenyl)borate 400 ml of toluene and $4 \times 10^{-4}$ mol of triisobutyl aluminum (2 mol/l toluene solution) was thoroughly stirred in an autoclave. To the autoclave were charged $1 \times 10^{-5}$ mol of isopropylidene(cyclopentadienyl-9-fluorenyl)zirconium dichloride (0.01 mol/l toluene solution) and $1 \times 10^{-5}$ mol of dimethylanilinium tetrakis(pentafluorophenyl)borate obtained in (1) above (0.01 mol/l toluene solution) in sequence, and the mixture was thoroughly stirred.

Next, propylene was continuously fed to the autoclave at 25° C. at a constant propylene pressure of 3 kg/cm², and reacted for one hour. After the completion of the reaction, the catalyst was deactivated by the addition of methanol. The resulting reaction mixture was filtered and dried under reduced pressure to obtain 54.5 g of syndiotactic polypropylene. The polymerization activity was 59.7 kg/g·Zr and 5.05 kg/g·Al.

The melting point of the polymer measured by the differential scanning calorimeter was 132° C., and the weight average molecular weight and the number average molecular weight as determined by the gel permeation chromatography based on polystyrene were $6.0 \times 10^4$ and $2.7 \times 10^4$, respectively. Tacticity determined by $^{13}$C-NMR at rrrr (racemi pentad) was 88%.

Comparative Example 1

(I) 2 g of lithium tetrakis(pentafluorophenyl)borate-diethyl ether complex ($2.92 \times 10^{-3}$ mol) obtained in Example 1, (II), was dissolved in 70 ml of water. 0.44 g ($2.78 \times 10^{-3}$ mol) of dimethylanilinium chloride was added to the solution and the mixture was stirred at room temperature for one hour. The solid thus obtained was thoroughly washed with water and hexane, and dried under reduced pressure. $^1$H-NMR was measured on the solid thus obtained to confirm that this solid was an about 1:1 complex of dimethylanilinium tetrakis(pentafluorophenyl)borate and diethyl ether. The yield was 2.3 g ($2.66 \times 10^{-3}$ mol).

(II) 400 ml of toluene and $4 \times 10^{-4}$ mol of triisobutyl aluminum (2 mol/l toluene solution) were thoroughly stirred in an autoclave. To the autoclave were charged $1 \times 10^{-5}$ mol of isopropylidene(cyclopentadienyl-9-fluorenyl)zirconium dichloride (0.01 mol/l toluene solution) and $1 \times 10^{-5}$ mol of dimethylanilinium tetrakis(pentafluorophenyl)borate-ethyl ether complex obtained in (I) above (0.01 mol/l toluene solution) in sequence, and the mixture was thoroughly stirred.

Next, propylene was continuously fed to the autoclave at a temperature of 25° C. or below at a constant propylene pressure of 3 kg/cm$^2$, and reacted for one hour. After the completion of the reaction, the catalyst was deactivated by the addition of methanol. The resulting reaction mixture was filtered and dried under reduced pressure to obtain 22.2 g of syndiotactic polypropylene. The polymerization activity was 24.3 kg/g·Zr and 2.06 kg/g·Al.

Comparative Example 2

(I) 2 g of lithium tetrakis(pentafluorophenyl)borate-diethyl ether complex ($2.92 \times 10^{-3}$ mol) obtained in Example 1, (II), was dissolved in 70 ml of water. 0.44 g ($2.78 \times 10^{-3}$ mol) of dimethylanilinium chloride was added to the solution and the mixture was stirred at room temperature for one hour. The solid thus obtained was thoroughly washed with water and hexane. This solid was dissolved in 20 ml of acetone, and the acetone solution was poured into a large quantity of water to re-precipitate the solid. The solid component was collected by filtration and thoroughly dried under reduced pressure. $^1$H-NMR was measured on the solid thus obtained to confirm that this solid was an about 1:1 complex of dimethylanilinium tetrakis(pentafluorophenyl)borate and acetone. The yield was 2.2 g ($2.57 \times 10^{-3}$ mol).

(II) 400 ml of toluene and $4 \times 10^{-4}$ mol of triisobutyl aluminum (2 mol/l toluene solution) were thoroughly stirred in an autoclave. To the autoclave were charged $1 \times 10^{-5}$ mol of isopropylidene(cyclopentadienyl-9-fluorenyl)zirconium dichloride (0.01 mol/l toluene solution) and $1 \times 10^{-5}$ mol of dimethylanilinium tetrakis(pentafluorophenyl)borate-acetone complex obtained in (1) above (0.01 mol/l toluene solution) in sequence, and the mixture was thoroughly stirred.

Next, propylene was continuously fed to the autoclave at a temperature of 25° C. or below at a constant propylene pressure of 3 kg/cm$^2$, and reacted for one hour. After the completion of the reaction, the catalyst was deactivated by the addition of methanol. The resulting reaction mixture was filtered and dried under reduced pressure to obtain 27.6 g of syndiotactic polypropylene. The polymerization activity was 30.2 kg/g·Zr and 2.56 kg/g·Al.

EXAMPLE 2

Production of lithium tetra(pentafluorophenyl)borate 180 ml of dry hexane, 180 ml of diethyl ether, and 24.7 g (0.1 mol) of bromopentafluorobenzene were charged into a reaction vessel, which had been displaced by nitrogen, and the mixture was cooled to −70° C., followed by the addition of 0.1 mol of n-butyl lithium dropwise while stirring. Then, 0.025 mol of boron trichloride was added dropwise at −70° C. The temperature was slowly raised to the room temperature. The precipitate was collected by filtration, washed with hexane, and dried to obtain 0.023 mol of Li[B(C$_6$F$_5$)$_4$]·O(C$_2$H$_5$)$_2$ containing LiCl. The yield based on bromopentafluorobenzene was 92%.

Comparative Example 3

The same procedure as in Example 2 was carried out, except that 360 ml of dry diethyl ether was used instead of 180 ml of dry hexane and 180 ml of diethyl ether. 0.016 mol of Li[B(C$_6$F$_5$)$_4$]·O(C$_2$H$_5$)$_2$ was thus obtained. The yield based on bromopentafluorobenzene was 64%.

EXAMPLE 3

Production of lithium tetra(pentafluorophenyl)borate 40 ml of dry hexane, 320 ml of diethyl ether, and 24.7 g (0.1 mol) of bromopentafluorobenzene were charged into a reaction vessel, which had been displaced by nitrogen, and the mixture was cooled to −70° C., followed by the addition of 0.1 mol of n-butyl lithium dropwise while stirring. Then, 0.025 mol of boron trichloride was added dropwise at −70° C. The temperature was slowly raised to the room temperature. The precipitate was collected by filtration, washed with hexane, and dried to obtain 0.022 mol of Li[B(C$_6$F$_5$)$_4$]·O(C$_2$H$_5$)$_2$ containing LiCl. The yield based on bromopentafluorobenzene was 88%.

EXAMPLE 4

Production of lithium tetra(pentafluorophenyl)borate 340 ml of dry hexane, 20 ml of diethyl ether, and 24.7 g (0.1 mol) of bromopentafluorobenzene were charged into a reaction vessel, which had been displaced by nitrogen, and the mixture was cooled to −70° C., followed by the addition of 0.1 mol of n-butyl lithium dropwise while stirring. Then, 0.025 mol of boron trichloride was added dropwise at −70° C. The temperature was slowly raised to the room temperature. The precipitate was collected by filtration, washed with hexane, and dried to obtain 0.020 mol of Li[B(C$_6$F$_5$)$_4$]·O(C$_2$H$_5$)$_2$ containing LiCl. The yield based on bromopentafluorobenzene was 80%.

EXAMPLE 5

The same procedure as in Example 4 was carried out, except that 340 ml of dry pentane, instead of dry hexane, and 20 ml of diisopropyl ether, instead of diethyl ether, were used, obtain 0.021 mol of Li[B(C$_6$F$_5$)$_4$]·O(C$_3$H$_7$)$_2$. The yield based on bromopentafluorobenzene was 84%.

EXAMPLE 6

Synthesis and purification of dimethylanilinium tetra(pentafluorophenyl)borate 1000 ml of diethyl ether and 49.4 g (0.4 mol) of bromopentafluorobenzene were charged into a reaction vessel which was displaced by nitrogen, and the mixture was cooled to −70° C., followed by the addition of 0.4 mol of n-butyl lithium dropwise while stirring. Then, 0.10 mol of boron trichloride was added dropwise at −70° C. The temperature was slowly raised to the room temperature. The precipitate was collected by filtration, washed with hexane, and dissolved into 200 ml of water. To this solution was added dropwise a solution of 0.10 mol of dimethylanilinium chloride dissolved in 50 ml of water to obtain 79 g of crude dimethylanilinium tetra(pentafluorophenyl)borate.

50 g of the crude dimethylanilinium tetra(pentafluorophenyl)borate was dissolved in 20 ml of methanol and the solution was added dropwise to 500 ml of water. 46 g of purified white dimethylanilinium tetra(pentafluorophenyl)borate was obtained by drying the product under vacuum.

EXAMPLE 7

Polymerization of styrene 6 l of styrene was charged into a 10 l container which was dried and displaced with nitrogen, and heated to 70° C. To this was added a solution of 9 mmol of triisobutyl aluminum, 150 μmol of purified dimethylanilinium tetra(pentafluorophenyl)borate, and 150 μmol of pentamethylcyclopentadienyltitaniumtrimethoxide dissolved in 75 ml of toluene, and the polymerization was carried out for 2 hours. The reaction was terminated by the addition of 1 l of methanol. Methanol was removed by filtration, and the produced polymer was dried under vacuum at 150° C. for 5 hours to obtain 4.1 kg of a polymer product.

This polymer was melted at 290° C. and injection molded 100 times using a mold made of iron at 140° C. The mold was allowed to leave for one day at RH 50% to confirm that no corrosion was produced. The molded product has an Y.I. value of 19.

Comparative Example 3

Styrene was polymerized in the same manner as in Comparative Example 2, except that crude dimethylanilinium tetra(pentafluorophenyl)borate was used, to obtain 4.0 kg of a polymer product. This polymer was injection molded. Corrosion was found in the mold. The Y.I value of the molded product was 25.

INDUSTRIAL APPLICABILITY

As illustrated above, tetrakisphenylborate obtained by the preparation and purification processes of the present invention is useful as a catalyst component for the polymerization of olefins, such as α-olefins and styrene monomers, or as a raw material for synthesizing the same. In particular, the tetrakisfluorophenylborate obtained by the present invention is excellent in its olefin polymerization activity, and owing to its high purity, is especially useful as a catalyst component for the polymerization of olefins or as a raw material for synthesizing the same.

We claim:

1. A process for preparing a tetrakisfluorophenylborate which comprises a first step in which the following reactions (1) and (2) are carried out in sequence and a second step in which the following reactions (3) and (4) are carried out in sequence, First Step:

$$3X^1C_6Y^1{}_5 + 3R^1M^1 \rightarrow 3M^1C_6Y^1{}_5 + 3R^1X^1 \qquad (1)$$

$$3M^1C_6Y^1{}_5 + BX^2{}_3 \rightarrow B(C_6Y^1{}_5)_3 + 3M^1X^2 \qquad (2)$$

Second Step:

$$X^1C_6Y^1{}_5 + R^2M^2 \rightarrow M^2C_6Y^1{}_5 + R^2X^1 \qquad (3)$$

$$M^2C_6Y^1{}_5 + B(C_6Y^1{}_5)_3 \rightarrow M^2B(C_6Y^1{}_5)_4 \qquad (4)$$

wherein $X^1$ and $X^2$ individually represent a halogen atom; Y represents a hydrogen atom or a fluorine atom, provided that 2 to 5 Ys among five Ys are fluorine atoms; $R^1$ and $R^2$ individually indicate an alkyl group or an aryl group; and $M^1$ and $M^2$ individually are an alkali or alkaline earth metal, or represent $R^3{}_2Al$, provided that $R^3$ is an alkyl group; and wherein the molar ratio of $M^1C_6Y^1{}_5$ and $BX^2{}_3$ in said reaction (2) is $3/2.5 \leq M^1C_6Y^1{}_5/BX^2{}_3 \leq 3/1.05$.

2. A process for preparing a tetrakisfluorophenylborate which comprises carrying out the following reactions (5) and (6) in sequence using an aliphatic hydrocarbon solvent, $$4X^3C_6Y^2{}_5 + 4R^4M^3 \rightarrow 4M^3C_6Y^2{}_5 + 4R^4X^3 \qquad (5)$$

$$4M^3C_6Y^2{}_5 + BCl_3 \rightarrow M^3B(C_6Y^2{}_5)_4 + 3M^3Cl_3 \qquad (6)$$

wherein $X^3$ represents a halogen atom; $Y^2$ represents a hydrogen atom or a fluorine atom, provided that 2 to 5 $Y^2$s among five $Y^2$s are fluorine atoms; $R^4$ indicates an alkyl group or an aryl group; and $M^3$ is an alkali or alkaline earth metal, or represents $R^5{}_2Al$, wherein $R^5$ is an alkyl group.

3. A process for preparing a tetrakisphenylborate which comprises carrying out the following reaction (7), $$4M^4-C_6Y^3{}_5 + BCl_3 \rightarrow M^4B(C_6Y^3{}_5)_4 \qquad (7),$$

wherein $M^4$ is an alkali or alkaline earth metal, or represents $R^6{}_2Al$, wherein $R^6$ is an alkyl group, and $Y^3$ represents a hydrogen atom or a-halogen atom, in a mixed solvent of ether and an aliphatic hydrocarbon.

4. A process for preparing a tetrakisfluorophenylborate comprising, adding a hydrocarbon solvent to the tetrakisfluorophenylborate to which a Lewis base is coordinated, and removing the Lewis base by concentrating or drying it under reduced pressure.

5. The process for preparing a tetrakisfluorophenylborate according to claim 4, wherein said tetrakisfluorophenylborate to which a Lewis base is coordinated is the tetrakisfluorophenylborate prepared by either one of the processes defined in claims 1–3.

6. A process for the purification of a tetrakisfluorophenylborate, which comprises dissolving the tetrakisfluorophenylborate in a solvent selected from the group consisting of ethers, ketones, alcohols and halogenated hydrocarbons, said solvent having an SP value of 15 or larger and 30 or smaller and depositing it from water or an aliphatic hydrocarbon solvent.

7. The process of claim 4, further comprising a purification step, which comprises dissolving the tetrakisfluorophenylborate in a solvent having an SP value of 15 or larger and 30 or smaller and depositing it from water or an aliphatic hydrocarbon solvent.

8. The process of claim 5, further comprising a purification step, which comprises dissolving the tetrakisfluorophenylborate in a solvent having an SP value of 15 or larger and 30 or smaller and depositing it from water or an aliphatic hydrocarbon solvent.

* * * * *

UNITED STATES PATENT AND TRADEMARK OFFICE
CERTIFICATE OF CORRECTION

PATENT NO.   : 5,600,005
DATED        : February 4, 1997
INVENTOR(S)  : Shoji NAGANUMA, et al.

It is certified that error appears in the above-indentified patent and that said Letters Patent is hereby corrected as shown below:

On the title page, Item [54] and the top of Column 1, the title should read:

--PROCESS FOR PRODUCING TETRAKISFLUOROPHENYLBORATE--

Signed and Sealed this

Sixth Day of May, 1997

Attest:

BRUCE LEHMAN

Attesting Officer

Commissioner of Patents and Trademarks